US00PP19646P2

(12) United States Plant Patent
Ilsink

(10) Patent No.: US PP19,646 P2
(45) Date of Patent: Jan. 20, 2009

(54) SHRUB ROSE PLANT NAMED 'INTERHAPPY'

(50) Latin Name: *Rosa hybrida*
Varietal Denomination: INTERhappy

(75) Inventor: Peter Ilsink, Leersum (NL)

(73) Assignee: Jackson & Perkins Wholesale, Inc., Hodges, SC (US)

( * ) Notice: Subject to any disclaimer, the term of this patent is extended or adjusted under 35 U.S.C. 154(b) by 0 days.

(21) Appl. No.: 11/986,558

(22) Filed: Nov. 20, 2007

(51) Int. Cl.
*A01H 5/00* (2006.01)

(52) U.S. Cl. ..... Plt./143

(58) Field of Classification Search ..... Plt./143
See application file for complete search history.

*Primary Examiner*—Annette H Para
(74) *Attorney, Agent, or Firm*—Klarquist Sparkman, LLP

(57) ABSTRACT

A shrub rose plant named 'INTERhappy', characterized by a combination of dark green, glossy foliage; flowers that are a yellow-orange color; and a compact form, particularly suitable as a groundcover.

1 Drawing Sheet

Genus and Species: *Rosa hybrida.*
Variety Denomination: 'INTERhappy'.

Origin of the Invention

The present invention relates to a new and distinct variety of a shrub rose plant named 'INTERhappy' which was originated by me as a cross of a pollen parent and a seed parent.

Background of the Invention

The primary objective of this breeding was to produce a new shrub rose variety.

Brief Summary of the Invention

The objective was substantially achieved as evidenced by a new shrub rose having a unique combination of characteristics that are outstanding in the new variety and that distinguish the new variety from its parents and other varieties of which the inventor is aware including dark green, glossy foliage, flowers that are a yellow-orange color (apricot/pink), and a compact form, particularly suitable as ground cover.

Asexual reproduction of this new variety by softwood cuttings, as performed at Wasco, Calif., shows that the foregoing characteristics and distinctions come true to form and are established and transmitted through succeeding propagations.

Comparison with Parents

'INTERhappy' has a more compact growth than the seed parent, which also had an orange flower color. The pollen parent had also compact growth, as 'INTERhappy', but the flower color of the pollen parent was pale yellow.

Comparison with Similar Variety

The inventor is not aware of any similar varieties with the flower color of 'INTERhappy'.

Brief Description of the Illustration

The accompanying illustration shows typical specimens of the vegetative growth and flowers of this new variety in different stages of development, depicted in color as nearly true as it is reasonably possible to make the same in a color illustration of this character.

Detailed Botanical Description

The following is a detailed description of my new rose cultivar with color descriptions using terminology in accordance with the Royal Horticultural Society (London) Colour Chart© 2001, except where ordinary dictionary significance of color is indicated.

Parentage:

*Seed parent.*—Unnamed seedling (B277-89) [B148-86×B269-86] (not patented).

*Pollen parent.*—'INTERdust' (U.S Plant Pat. No. 10,240).

FLOWER

Observations of the new variety were made from January 2005 to October 2007. The observations set forth below are of plants of the new variety that are three years of age and grown in a garden environment at Somis, Calif.

Blooming Habit: Continuous.

Bud:

*Size.*—About 18–20 mm and 10–12 mm in diameter when the petals start to unfurl.

*Form.*—The bud form is long, pointed ovoid.

*Color.*—When sepals first divide, bud color is Red Group 40D. When half blown, the upper sides of the petals are Yellow-Orange Group 23C with center vein of Red Group 40D approximately 2–3 mm in width and the lower sides of the petals are Red Group 40D with occasional Yellow-Orange Group 23C on margins.

*Sepals.*—Color: Upper surface: Yellow-Green Group 147D. Lower surface: Yellow-Green Group 144C with prominent center vein of Green Group 150C. Length: 25–30 mm. Width: 5–7 mm. Shape: Subulate. Surface: Upper: Ciliolate. Lower: Smooth. There are three lightly appendaged sepals. There are two unappendaged sepals with glandular edges.

*Receptacle.*—Color: Yellow-Green Group 144C. Shape: Pear. Size: Small, about 6–7 mm long×6–7 mm wide. Surface: Smooth, few hairs.

*Peduncle.*—Length: Short, averaging about 10–20 mm. Surface: Prickly. Color: Yellow-Green Group 144C, new growth Greyed Red Group 178B. Strength: Stiff.

Bloom:

*Size.*—Small. Average open diameter is about 4 cm.

*Borne.*—In clusters of 7–13 blooms having pyramidal shape.

*Stems.*—Strength: Normal. Average length is about 20–30 cm with a diameter of 6–8 mm.

*Form.*—When first open: Flat. Permanence: Outer petals edges curl slightly.

*Petalage.*—Number of petals under normal conditions: 6.

*Color.*—The upper sides of the petals are Yellow-Orange Group 23C with prominent center vein of Red Group 40D. The reverse sides of the petals are Red Group 40D with occasional Yellow-Orange Group 23C on margins. The base of the petals has Yellow Group 13B. The major color on the upper sides is Yellow-Orange Group 23C and Red Group 40D.

*Discoloration.*—The general tonality at the end of the first day is Yellow-Orange Group 23C and Red Group 40D. At the end of the third day: Red Group 56A and Red Group 55B. At Day 5, Red Group 56C and Red Group 55C.

*Fragrance.*—None observed in Somis, Calif.

Petals:

*Thickness.*—Thick.

*Surface texture.*—Smooth.

*Shape.*—Obovate.

*Margin.*—Entire.

*Apex shape.*—Cuspidate.

*Base shape.*—Rounded.

*Form.*—Flat, slightly quilled.

*Arrangement.*—Imbricated.

*Petaloids.*—None.

*Persistence.*—Petals drop off cleanly before drying.

*Lastingness.*—On the plant: Short (about 3–4 days). As a cut flower: Short (about 3–4 days).

Reproductive Parts:

*Stamens.*—Number: 55–60. Length: 7–8 mm. Anthers: Length: 1–2 mm. Color: Yellow-Orange Group 21C. Arrangement: Regular around styles. Filaments: Color: Yellow Group 13B. Length: 5–7 mm. Pollen: Color: Yellow-Orange Group 22A.

*Pistils.*—Number: 20. Length: 3 mm. Styles: Color: Green-White Group 157B. Length: 2 mm. Stigmas: Color: Green-White Group 157B with a slight overlay of Greyed-Purple Group 186D on the upper portion. Length: 1 mm.

*Hips.*—Immature: Color: Yellow-Green Group 146B. Mature: Color: Orange-Red Group 34A. Shape: Globose. Size: 15 mm long×15 mm in diameter. Seeds: 6 to 10 seeds per hip typical.

PLANT

*Form.*—Shrub.

*Growth.*—Vigorous, branching, sprawling.

*Age to Maturity.*—Two years.

*Mature plant.*—Height: Typically to about 60 cm in Somis, Calif. Width: Typically to about 90 cm in Somis, Calif.

*Rootstock.*—On own roots.

Foliage: Number of leaflets on normal mid-stem leaves: 5 or 7.

*Size.*—Medium. 90 mm long×55 mm wide.

*Quantity.*—Abundant.

*Color.*—New foliage: Upper side: Greyed-Red Group 178B but quickly turning green. Lower side: Greyed-Red Group 178B but quickly turning green. Old foliage: Upper side: Green Group 139A. Lower side: Green Group 137C.

Leaflets:

*Size.*—About 25 mm long×15 mm wide.

*Shape.*—Oval.

*Base shape.*—Oblique to rounded.

*Apex shape.*—Acuminate.

*Texture.*—Glossy, smooth.

*Edge.*—Serrated.

*Serrations.*—Single.

*Petiole.*—Color: Lower surface: Yellow-Green Group 146C. Upper Surface: Green Group 137B.

*Petiole rachis.*—Color: Lower surface: Yellow-Green Group 146C. Upper Surface: Green Group 137B. Underside: Rough with prickles.

*Auricles.*—None observed.

*Stipules.*—Length: 17 mm, serrated, glandular.

*Disease resistance.*—Resistant to mildew and rust and susceptible to blackspot under normal growing conditions.

*Pest resistance.*—None observed.

*Vein color.*—Green Group 137B.

*Venation pattern.*—Reticulate.

Wood:

*New wood.*—Color: Greyed-Purple Group 183A briefly then Turning to Yellow-Green Group 146D. Bark: Smooth.

*Old wood.*—Color: Yellow-Green Group 146B. Bark: Smooth.

Prickles:

*Quantity.*—Ordinary, on main canes from base: 20–25 per 15 cm of wood. Ordinary, on laterals from main canes: 20–25 per 15 cm of wood.

*Form.*—Straight, to very slightly hooked downward.

*Length.*—7–8 mm.

*Color when young.*—Greyed-Purple Group 183C.

*Color when mature.*—Greyed-Orange Group 177B.

Small Prickles:

*Quantity.*—On main stalks: None. On laterals: None.

Winter Hardiness: Hardy to Zone 5.

I claim:

1. A new and distinct variety of shrub rose plant of the 'INTERhappy' variety, substantially as herein shown and described.

* * * * *

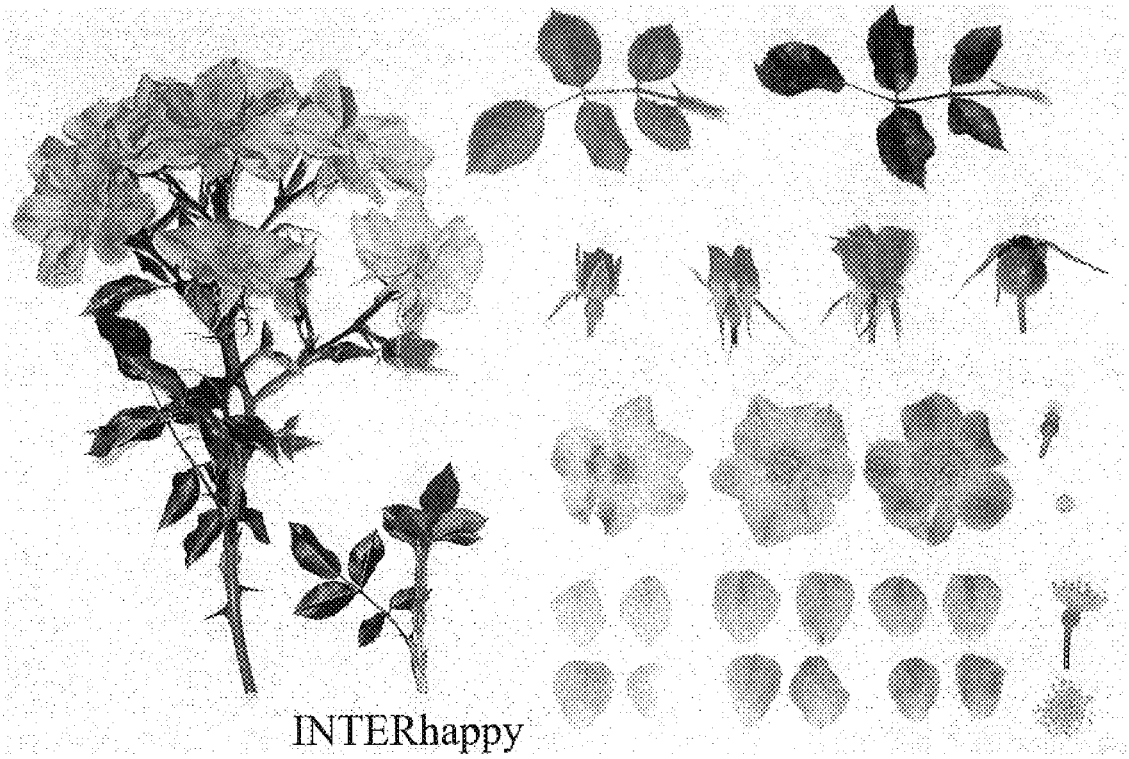
INTERhappy